US00PP12250P2

(12) United States Plant Patent
Drewlow

(10) Patent No.: US PP12,250 P2
(45) Date of Patent: Dec. 4, 2001

(54) STREPTOCARPUS PLANT NAMED 'ARTEMIS'

(75) Inventor: Lyndon W. Drewlow, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/573,404

(22) Filed: May 18, 2000

(51) Int. Cl.[7] ..... A01H 5/00

(52) U.S. Cl. ..... Plt./333

(58) Field of Search ..... Plt./333

*Primary Examiner*—Bruce R. Campell
*Assistant Examiner*—Kent L. Bell
(74) *Attorney, Agent, or Firm*—Webb Ziesenheim Logsdon Orkin & Hanson, P.C.

(57) ABSTRACT

A Streptocarpus plant named Artemis characterized by the combined characteristics of lavender-purple flowers which are long-lasting, non-shattering, and continuously bloom under low light conditions of winter and high temperatures of summer.

2 Drawing Sheets

The present invention relates to a new and distinct cultivar of Streptocarpus plant, botanically known as *Streptocarpus× hybridus,* and known by the cultivar name Artemis. 'Artemis' was developed through controlled breeding by crossing Mikkelsen Seedling No. 92-153-7 (seed parent) (unpatented) with Mikkelsen Seedling No. 92-176-3 (pollen parent) (unpatented). The seed and pollen parents are proprietary breeding lines which have not been sold or made publicly available in this country.

Asexual reproduction of leaf cuttings has shown that the unique features of this new Streptocarpus are stabilized and are reproduced true to type in successive propagations. The plant was first propagated in Ashtabula, Ohio.

The following characteristics distinguish the new Streptocarpus from other cultivated Streptocarpus of this type known to the inventor. The characteristics are described with comparative reference to the cultivars Demeter (unpatented) and Marna (U.S. Plant Pat. No. 4,524).

1. 'Artemis' has lavender-purple colored flowers of Violet Group 83B with netted areas of Violet Group 83A while 'Demeter' has colored flowers of Violet Group 87A with netting of White Group 155C and 'Marna' has colored flowers of Violet-Blue Group 89A.

2. 'Artemis' has a white throat on upper two petals and a lavender-purple throat on lower three petals while 'Demeter' has a white throat with violet streaking on all five petals and 'Marna' has a yellow throat on lower three petals and white throat on upper two petals.

3. 'Artemis' has smaller flowers at 45 to 50 mm in diameter than 'Demeter' at 50 to 55 mm and 'Marna' at 60 to 65 mm.

4. 'Artemis' has leaves that average 15 to 18 cm long and 5.5 to 6.5 cm wide while 'Demeter' has leaves 15 to 18 cm long and 4.5 to 5 cm wide and the leaves of 'Marna' are longer at 23 to 25 cm and 5.5 to 6.5 wide.

5. 'Artemis' is similar in height to 'Demeter' at 13 to 15 cm but shorter than 'Marna' at 18 to 20 cm.

6. 'Artemis' is intermediate in sepal coloration with a light red-purple cast and 'Demeter' having a heavy red-purple cast, and 'Marna' having green sepals.

7. 'Artemis' has a pistil that is white with violet cast and a white style, while 'Demeter' has both with a violet cast and 'Marna' has both being white.

8. The netting pattern of 'Artemis' is intermediate between 'Demeter' with heavy white netting and 'Marna' having a solid color.

The accompanying colored photographs illustrate the overall appearance of the cultivar taken as a face view of the plant and showing the colors as true as it is reasonably possible to obtain in colored reproductions of this type.

Figure 1:
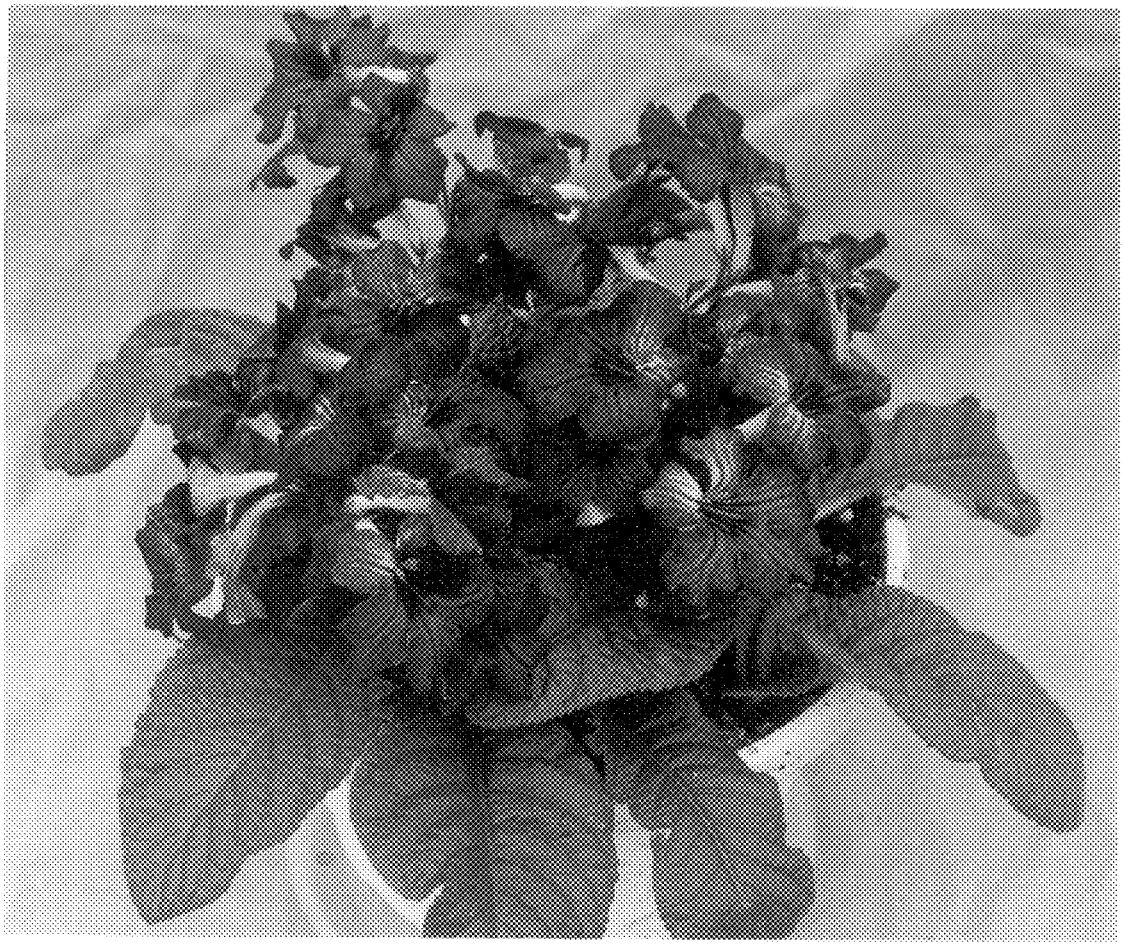
FIG. 1 is an overall view of the plant.
Figure 2:
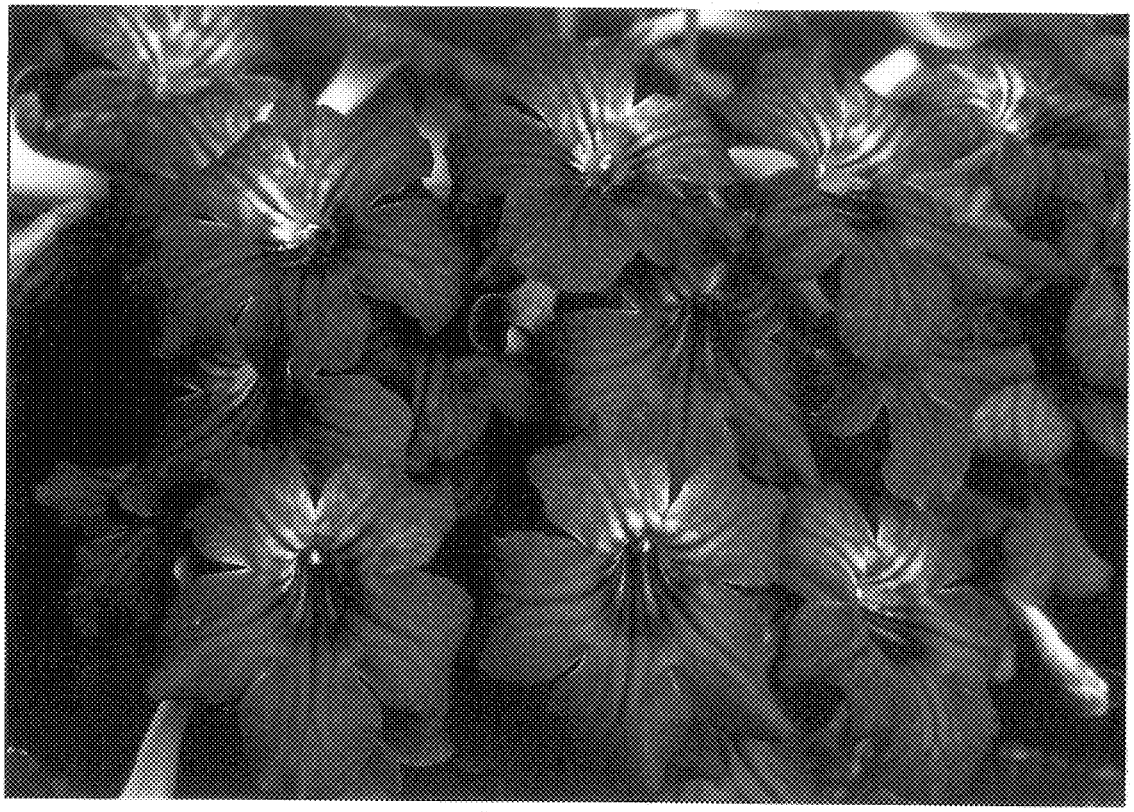
FIG. 2 is a close-up view of the flowers.

The following is a detailed description of my new cultivar, based on plants produced in greenhouses in Lompoc, Calif. during the Winter season of the year. Plants were grown in 10 cm pots and measurements were taken 12 weeks after rooted cuttings were planted. Height measurements were taken from the soil line of the container. The plants were grown at 16° C. night temperatures 2500–3500 foot candles of light and 200 ppm nitrogen, 75 ppm potassium and 200 ppm phosphorous nutritional levels, with trace elements added. Habit of growth, foliage coloration, size of leaves and flower size will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 92-153-7 and male parent Mikkelsen Seedling No. 92-176-3.

Propagation:

(*A*) *Type cutting.*—Leaf.

(*B*) *Time to develop.*—8 weeks at 22° C. summer; 8 weeks at 22° C. winter.

(*C*) *Root description.*—Fine, abundant, fibrous.

Plant description:

*Habit and form of growth.*—Vigorous, leaves are in a rosette extending from a crown at soil line. Leaves form around plant to produce a symmetrical plant with flower stalks forming at basal area of midrib of each mature leaf; flowers are carried above foliage. Fruit/seed not produced.

*Height.*—13 to 15 cm from soil line.

*Foliage description.*—Spread: 25 to 30 cm at maturity. (1) Size: 15 to 18 cm in length and 5.5 to 6.5 cm in width at maturity. (2) Quantity: More than 15 leaves on a mature plant. (3) Shape: Elliptical. (4) Texture: Lower surface rugose with veins protruding and pubescent; upper surface rugose and pubescent. (5)

Margin: Crenate. (6) Color: Young foliage top side is Yellow-Green Group 146A, underside is Yellow-Green Group 147C. Mature foliage top side is Yellow-Green Group 147A, underside is Yellow-Green Group 148B. (7) Ribs and veins: Pinnate. (8) Rib and vein color: Underside Yellow-Green Group 147C. (9) Leaf tips: Acute to rounded. (10) Leaf Base: Acute. (11) Leaves are stalked and have petioles. The petioles are 20 mm long, 10 mm in diameter, and have a Yellow-Green Group 146A color with a Red-Purple Group 184D cast.

Flower:

*Flower opening.*—Open one at a time on individual flower stalks.

*Fully expanded.*—45 to 50 mm in diameter.

*Stem.*—Single, Yellow-Green Group 146A with a Red-Purple Group 184D cast, especially at base end, length is typically 10 cm and diameter is typically 2 mm, pubescent, several from a leaf midrib.

*Form.*—Funnel-shaped, corolla cylindrical 5 lobed, lobes orbicular to obovate with 2 upper petals smaller than the 3 bottom petals. Flower opens flat and then become ruffled. Calyx deeply five-parted with no tube.

*Flower bud.*—Immature bud hangs downward, raising as matures. At maturity is 23 to 25 mm long with 5 sepals in calyx folded over basal end. The bud diameter is 4 mm and the bud shape is linear to oblong and tublar. The sepals have a length of 6 mm, a width of 1 mm, an entire margin, an acute apex, a truncate base and a Yellow-Green Group 146A color.

*Flowers borne.*—In clusters of usually 2 to 4 flowers per flower stalk, with 2 flowers being the most common on a mature plant carried above the foliage. Pedicels of upper flowers on stalk are 5 to 6 mm long and 6 to 7 mm long on lower flowers, and have a Yellow-Green Group 146A color.

*Quantity of flowers.*—Mature plant can have 15 or more flower stalks with up to 4 flowers open per stalk.

*Permanence.*—Approximate time period for bloom lastingness is 10 to 12 days.

Color:

*Tonality from a distance.*—Purple flower with light lavender highlights and white throat with purple streaking.

*Front of petals.*—Violet Group 83B with Violet Group 83A and White Group 155D in the throat.

*Reverse of petals.*—White Group 155C in tubular area going to Violet Group 83D in the open petal part.

*Throat.*—White Group 155C with Violet Groups 83A and 83B streaking.

*Discoloration.*—White area increases and Violet Group 83A veining becomes more pronounced.

Petals:

*Texture.*—Satin.

*Appearance.*—Individual lobed with slightly crenate margins, top 2 petals are reflexed and smaller than the bottom petals which are flat and slightly contorted. Length is 25 mm fused and 20 mm not fused. Width is 20 mm. The margin is entire and the apex is obtuse to rounded.

*Arrangement.*—Circular in shape with deep cuts between the petals, little overlap of petals.

*Persistence.*—Will dry on the plant before finally dropping off.

*Fragrance.*—None.

Reproductive organs:

*Stamens.*—2 fertile interconnected by the anthers and 2 sterile and barely visible. (1) Anther: Flat in shape, white in color. (2) Filament: White with violet case, 2 fertile free standing for 7 mm. (3) Pollen: Moderate, white color.

*Pistils.*—Number: 1 (1) Stigma shape: Flattened with reflexed tips. Color: White-violet case. Size: 3 mm in diameter. (2) Style: Color: White. Size: 6 mm in diameter. (3) Ovaries: Number: 1 with over 500 ovules. Size: 10 to 12 mm in diameter on a receptive pistil. Color: Green with red-purple cast.

Disease resistance: No disease problems seen to date.

OTHER IMPORTANT CHARACTERISTICS

1. 'Artemis' has numerous short leaves in a rosette instead of a few large leaves that characterize many older Streptocarpus cultivars. This results in a very floriferous plant with flowers clustered in middle of green foliage making an attractive 15 cm plant.

2. Flowers are long-lasting, non-shattering and leaves are small and pliable making this cultivar easy to ship.

3. 'Artemis' has shown the ability to flower year round during higher temperatures of summer and lower light levels of winter under greenhouse conditions.

4. 'Artemis' does not foliar spot when watered with 10° C. water and tolerates fairly high light levels (2500 foot candles) without the leaves bronzing.

I claim:

1. A new and distinct cultivar of Streptocarpus plant named Artemis, as illustrated and described.

* * * * *